(12) United States Patent
Kluin et al.

(10) Patent No.: US 9,523,652 B2
(45) Date of Patent: Dec. 20, 2016

(54) METHOD AND APPARATUS FOR MEASURING MOISTURE CONTENT

(75) Inventors: Julie A. Kluin, Sioux Falls, SD (US); Brandon L. McLellan, Sioux Falls, SD (US)

(73) Assignee: POET Research, Inc., Sioux Falls, SD (US)

( * ) Notice: Subject to any disclaimer, the term of this patent is extended or adjusted under 35 U.S.C. 154(b) by 851 days.

(21) Appl. No.: 13/267,656

(22) Filed: Oct. 6, 2011

(65) Prior Publication Data

US 2012/0086429 A1    Apr. 12, 2012

Related U.S. Application Data

(60) Provisional application No. 61/391,481, filed on Oct. 8, 2010.

(51) Int. Cl.
*G01N 27/00* (2006.01)
*G01N 27/22* (2006.01)

(52) U.S. Cl.
CPC .................. *G01N 27/223* (2013.01)

(58) Field of Classification Search
CPC .................. G01N 2033/245; G01N 33/246
USPC ......... 324/71.1, 61, 65, 75, 689, 694; 73/73, 73/864.31
See application file for complete search history.

(56) References Cited

U.S. PATENT DOCUMENTS

| | | | | |
|---|---|---|---|---|
| 2,723,557 A | * | 11/1955 | Ohlheiser | 73/73 |
| 2,856,156 A | * | 10/1958 | Young | 173/26 |
| 3,252,546 A | * | 5/1966 | Allin, Jr. | B62D 33/06 180/89.12 |
| 3,493,246 A | * | 2/1970 | Hornung | A01B 73/065 172/456 |
| 3,789,671 A | * | 2/1974 | Larson | 73/864.32 |
| 3,803,570 A | * | 4/1974 | Barlow et al. | 318/643 |
| 3,870,951 A | * | 3/1975 | Brown et al. | 324/689 |
| 4,037,476 A | * | 7/1977 | McCrabb | 73/864.31 |
| 4,064,753 A | * | 12/1977 | Sun | G01F 23/263 324/684 |
| 4,332,301 A | * | 6/1982 | Jonell | 175/50 |
| 4,399,404 A | * | 8/1983 | Resh | 324/689 |
| 4,514,127 A | * | 4/1985 | Maier | A01D 87/127 16/86 C |
| 4,616,515 A | * | 10/1986 | Dancoine | 73/864.31 |
| 4,757,252 A | * | 7/1988 | Maltby et al. | 324/687 |
| 4,800,765 A | * | 1/1989 | Nelson | G01N 1/08 73/863.86 |
| 4,929,904 A | * | 5/1990 | Bohman et al. | 324/696 |
| 5,076,372 A | * | 12/1991 | Hellbusch | 175/20 |
| 5,356,214 A | * | 10/1994 | Styles | B01F 7/161 366/285 |
| 5,394,949 A | * | 3/1995 | Wright et al. | 175/20 |

(Continued)

*Primary Examiner* — Jermele M Hollington
*Assistant Examiner* — Giovanni Astacio-Oquendo
(74) *Attorney, Agent, or Firm* — Amin, Turocy & Watson, LLP

(57) ABSTRACT

An apparatus for measuring moisture content of biomass is disclosed. The apparatus comprises a probe apparatus and a mechanism that inserts the probe apparatus into the biomass. The probe apparatus measures a capacitance of the biomass. In accordance with an embodiment, the probe apparatus is mounted on the mechanism. In an embodiment, the mechanism positions the probe apparatus over the biomass. According to an embodiment, the mechanism inserts the probe apparatus into the biomass as the biomass is being transported in a trailer.

20 Claims, 7 Drawing Sheets

(56) References Cited

U.S. PATENT DOCUMENTS

| | | | |
|---|---|---|---|
| 5,442,293 A * | 8/1995 | Lange | 324/332 |
| 5,479,104 A * | 12/1995 | Cambell | 324/690 |
| 5,703,928 A * | 12/1997 | Galloway | G01R 1/07 |
| | | | 324/515 |
| 5,992,231 A * | 11/1999 | Mulder | G01F 23/24 |
| | | | 73/304 C |
| 6,076,396 A * | 6/2000 | Dadachanji et al. | 73/73 |
| 7,575,069 B2 * | 8/2009 | Pavlik | E21B 7/027 |
| | | | 173/185 |
| 2002/0075009 A1 * | 6/2002 | Butler | 324/534 |
| 2003/0118832 A1 * | 6/2003 | Skaling et al. | 428/412 |
| 2005/0172701 A1 * | 8/2005 | Loucks et al. | 73/73 |
| 2009/0205363 A1 * | 8/2009 | de Strulle | 62/533 |

* cited by examiner

METHOD AND APPARATUS FOR MEASURING MOISTURE CONTENT

CROSS-REFERENCE TO RELATED APPLICATIONS

This application claims the benefit of U.S. Provisional Application Ser. No. 61/391,481, filed Oct. 8, 2010, and entitled "METHOD AND APPARATUS FOR MEASURING MOISTURE CONTENT", the entirety of which is incorporated herein by reference.

FIELD

The subject disclosure relates to an apparatus for measuring moisture. The subject disclosure also relates to an apparatus for measuring moisture content of biomass bales.

BACKGROUND

Ethanol can be produced from grain-based feedstocks (e.g. corn, sorghum/milo, barley, wheat, etc.), from sugar (e.g. from sugar cane, sugar beets, etc.), and from biomass (e.g. from lignocellulosic feedstocks such as switchgrass, corn cobs and stover, wood, other plant material, or algae).

Biomass comprises plant matter that can be suitable for direct use as a fuel/energy source or as a feedstock for processing into another bioproduct (e.g., a biofuel such as cellulosic ethanol) produced at a biorefinery (such as an ethanol plant). Biomass may comprise, for example, corn cobs and stover (e.g., stalks and leaves) made available during or after harvesting of the corn kernels, fiber from the corn kernel, switchgrass, farm or agricultural residue, wood chips or other wood waste, algae, and other plant matter. In order to be used or processed, biomass is harvested and collected from the field and transported to the location where it is to be used or processed. An example of a way to efficiently collect and transport biomass is biomass bales. Biomass may be collected and baled during or after grain harvest.

In a conventional ethanol plant producing ethanol from corn, ethanol is produced from starch. In contrast, in a biorefinery configured to produce ethanol from biomass such as cellulosic feedstocks, ethanol is produced from lignocellulosic material (e.g. cellulose and/or hemi-cellulose). The biomass is prepared so that sugars in the cellulosic material (such as glucose from the cellulose and xylose from the hemi-cellulose) can be accessed and fermented into a fermentation product that comprises ethanol (among other things). The fermentation product is then sent to the distillation system where the ethanol is recovered by distillation and dehydration. Other bioproducts such as lignin and organic acids may also be recovered as co-products. Determination of how to more efficiently prepare and treat the biomass for production into ethanol will depend upon (among other things) the form and type or composition of the biomass.

For example, the moisture content of the biomass bales can vary considerably (e.g., from less than 20 percent to more than 40 percent) based on harvest conditions, harvest timing, storage conditions, and the like. Knowledge of the moisture content of the bales brought to the facility directly affects the amount of water introduced into the ethanol production process. Likewise, knowing the moisture content of the bales at the time of purchase is beneficial because the price of the bales is usually set on a dry matter basis. It would also be beneficial for farmers to be able to monitor the moisture content of their bales in storage.

In addition to use in a cellulosic ethanol production facility, biomass may be utilized in a wide variety of downstream applications, such as feedstock for farm animals, fertilizer and composite materials, ground cover, and the like. In each of these applications, determining the moisture content of the biomass may be particularly important for assessing quality and/or pricing for the biomass product.

Many assays exist for determining moisture content of plant materials, often comprising measuring weight loss during drying in an oven, for example. Measuring moisture content using an oven usually consumes considerable time and is not a portable method. Other methods include, for example, Near Infrared Spectroscopy (NIR), which requires expensive and sensitive equipment and is also not very suitable for field use.

SUMMARY

The subject disclosure relates to an apparatus for measuring moisture content of biomass. The apparatus comprises a probe apparatus and a mechanism that inserts the probe apparatus into the biomass. The probe apparatus measures moisture content of the biomass. The measurement may be made by sensing capacitance of the biomass, conductance through biomass material, microwave absorption, or other reasonable method of measuring moisture. In accordance with an embodiment, the probe apparatus is mounted on the mechanism. In an embodiment, the mechanism positions the probe apparatus over the biomass. According to an embodiment, the mechanism inserts the probe apparatus into the biomass as the biomass is being transported in a trailer.

The subject disclosure also relates to a system for measuring moisture content. The system comprises means for reading a moisture content of biomass. The system also comprises means for positioning the means for reading over the biomass and means for inserting the means for reading into the biomass. According to an embodiment, the means for reading comprises a single probe. According to some embodiments, the means for reading comprises multi-probes.

The subject disclosure further relates to a method for measuring moisture content of biomass. The method comprises providing a device that can take a reading that is indicative of a moisture content of the biomass. The method also comprises positioning the device over the biomass, inserting the device into the biomass, and obtaining the reading that is indicative of the moisture content. In accordance with some embodiments, providing the device comprises providing a device that includes at least one probe.

DESCRIPTION OF THE EMBODIMENTS

The subject disclosure relates to systems and methods for measuring moisture content of biomass. Biomass may be utilized in a number of downstream applications including as a fuel source, livestock feed, compost/fertilizer, groundcover, cellulosic ethanol production, among other known or future known applications. Much of the disclosure will center around the application of biomass for use as a raw material for cellulosic ethanol production. This detailed disclosure of biomass for use in ethanol production is intended to merely illustrate an example application for the use of biomass. These examples are not intended in any way to limit the scope of the embodiments to biomass for any particular purpose.

In a similar vein, much of the biomass discussed in this application includes corn cob and stover (e.g., leaves and stalks) biomass. While corn biomass is plentiful, and of particular interest in use for some applications of cellulosic ethanol production, the subject disclosure is intended to be equally applicable to all sources of biomass including, for example, wood by-products, switch grass, hemp, peat, virtually any plant material, and algae including seaweeds. The discussion of biomass including corn plant derived materials are, thus, intended to be entirely for clarification and exemplary purposes.

An aspect provides an apparatus for measuring the moisture content of biomass in a relatively less expensive, rapid, and portable manner. Various aspects also provide an apparatus for measuring the moisture content of biomass bales. Further, the disclosed aspects provide an apparatus that can measure the moisture content of biomass bales quickly and can be used at a field or at a truck receiving site.

Figure 1:
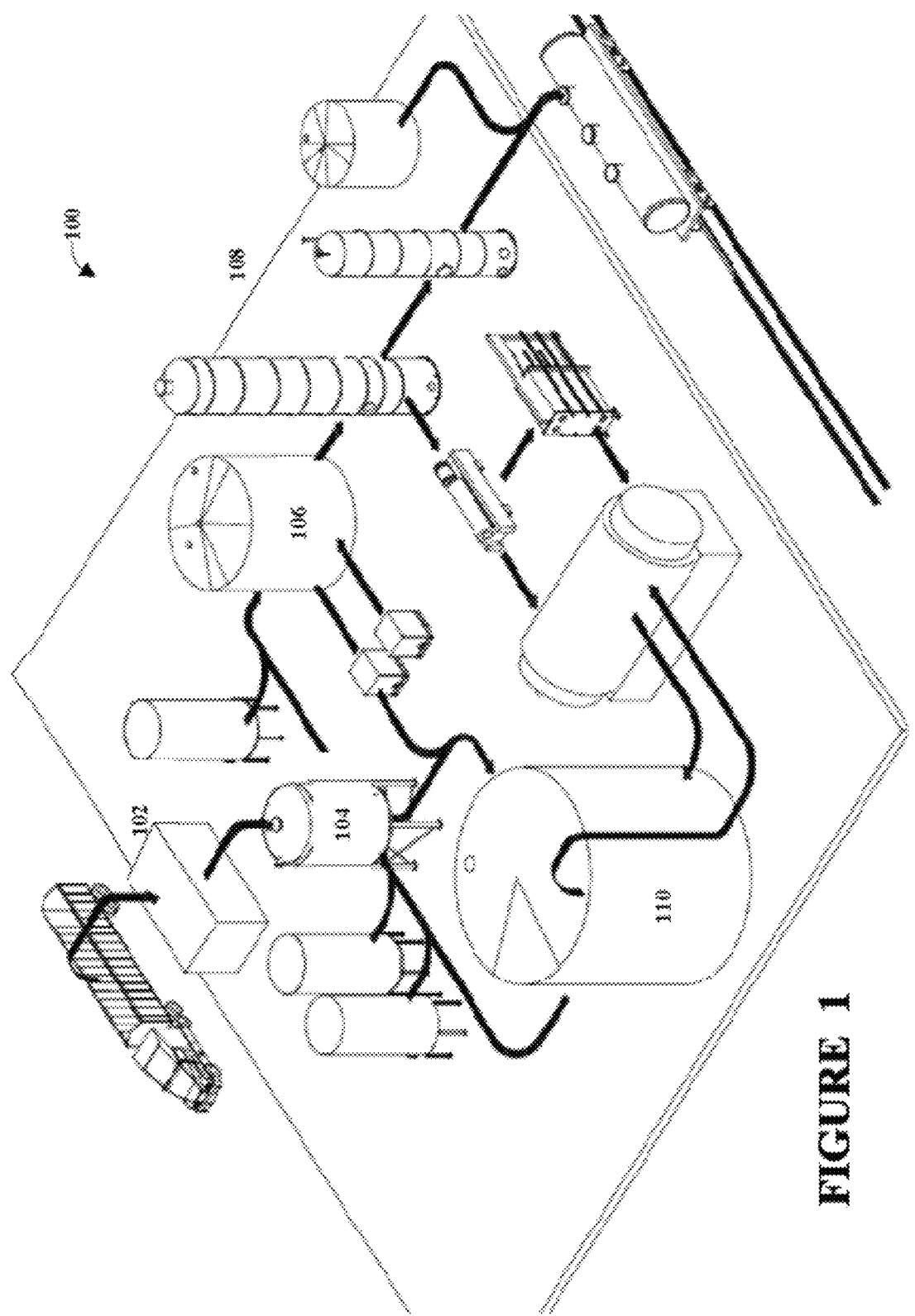
FIG. 1 is a perspective view of a biorefinery comprising a cellulosic ethanol production facility.

Referring to FIG. 1, a biorefinery 100 configured to produce ethanol from biomass is shown.

According to an exemplary embodiment, the biorefinery 100 is configured to produce ethanol from biomass in the form of a lignocellulosic feedstock such as plant material from the corn plant (e.g., corn cobs and corn stover). Lignocellulosic feedstock such as lignocellulosic material from the corn plant comprises cellulose (from which C6 sugars such as glucose can be made available) and/or hemicellulose (from which C5 sugars such as xylose and arabinose can be made available).

As shown in FIG. 1, the biorefinery 100 comprises an area where biomass is delivered and prepared to be supplied to the cellulosic ethanol production facility. The cellulosic ethanol production facility comprises an apparatus for preparation 102, pre-treatment 104 and treatment of the biomass into treated biomass suitable for fermentation into fermentation product in a fermentation system 106. The facility comprises a distillation system 108 in which the fermentation product is distilled and dehydrated into ethanol. As shown in FIG. 1, the biorefinery may also comprise a waste treatment system 110 (shown as comprising an anaerobic digester and a generator). According to other alternative embodiments, the waste treatment system may comprise other equipment configured to treat, process, and recover components from the cellulosic ethanol production process, such as a solid/waste fuel boiler, anaerobic digester, aerobic digester or other biochemical or chemical reactors.

Figure 2:
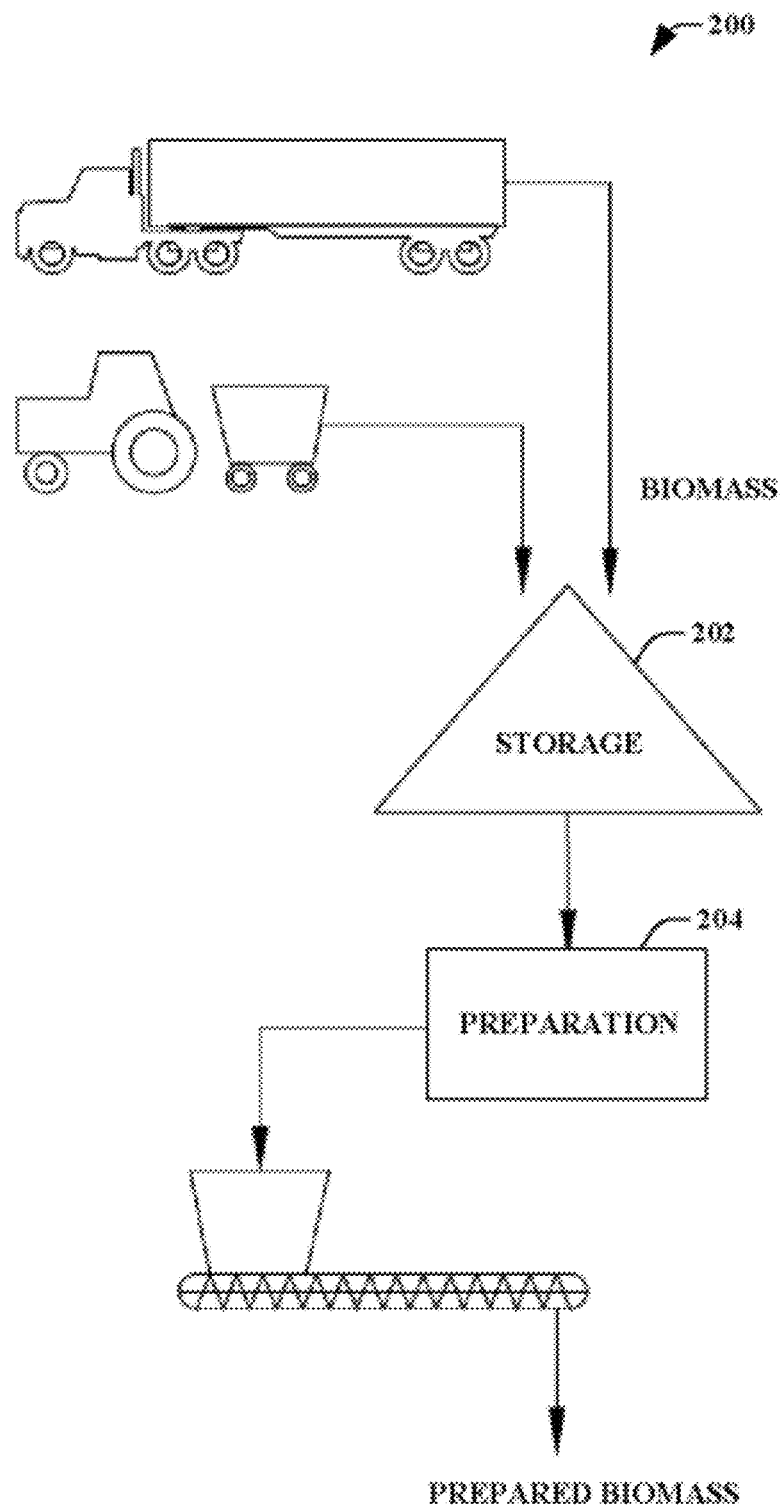
FIG. 2 is a schematic diagram of a system for receipt and preparation of biomass for a cellulosic ethanol production facility.

Referring to FIG. 2, a system 200 for preparation of biomass delivered to the biorefinery is shown. The biomass preparation system 200 may comprise an apparatus for receipt/unloading of the biomass, cleaning (e.g., removal of foreign matter), grinding (e.g., milling, reduction, or densification), transport, and conveyance for processing at the plant. According to an exemplary embodiment, biomass in the form of corn cobs and stover may be delivered to the biorefinery and stored (e.g., in bales, piles or bins, etc.), shown as storage 202, and managed for use at the facility. According to an embodiment, the biomass may comprise at least 20 to 30 percent corn cobs (by weight) with corn stover and other matter. According to other exemplary embodiments, a preparation system 204 of the biorefinery may be configured to prepare any of a wide variety of types of biomass (e.g., plant material) for treatment and processing into ethanol and other bioproducts at the plant.

Figure 3:
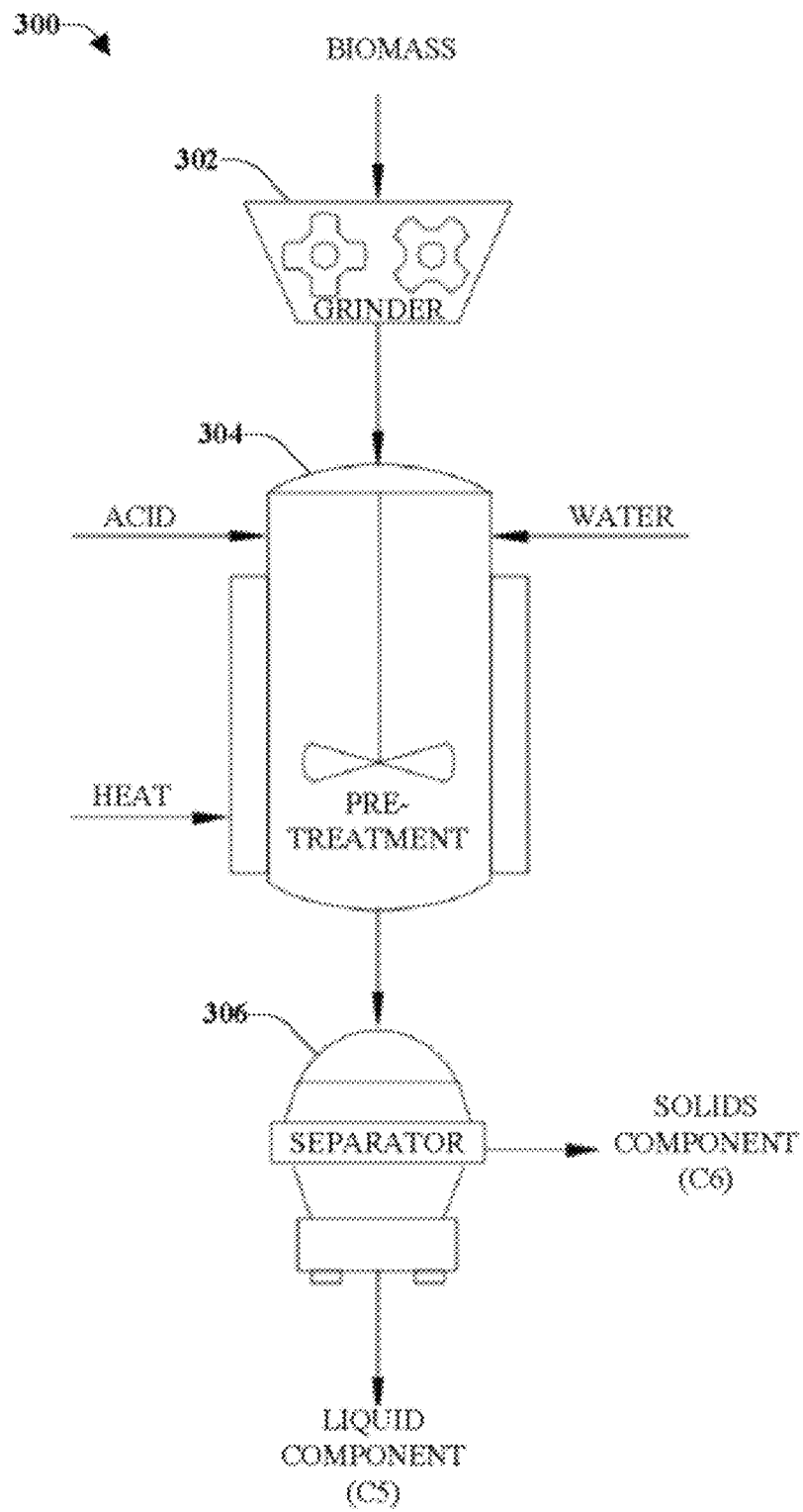
FIG. 3 is a schematic block diagram of an apparatus used for preparation, pre-treatment, and separation of biomass.

FIG. 3 illustrates the apparatus 300 used for preparation, pre-treatment, and separation of lignocellulosic biomass according to an exemplary embodiment. As shown, biomass is prepared in a grinder 302 (e.g., grinder or other suitable apparatus or mill). Pre-treatment 304 of the prepared biomass is performed in a reaction vessel (or set of reaction vessels) supplied with prepared biomass and acid/water in a predetermined concentration (or pH) and other operating conditions. In this example downstream use for biomass, the moisture content of the starting biomass material may be particularly important in that it may vary the amount of water and/or acid needed to properly pre-treat the biomaterial. The pre-treated biomass can be separated in a centrifuge 306 into a liquid component (C5 stream comprising primarily liquids with some solids) and a solids component (C6 stream comprising liquids and solids such as lignin and cellulose from which glucose can be made available by further treatment).

According to an embodiment, in the pre-treatment system an acid, such as sulfuric acid, hydrochloric acid, nitric acid, phosphoric acid, acetic acid, etc. (or a formulation/mixture of acids), can be applied to the prepared biomass to facilitate the breakdown of the biomass for separation into the liquid component (C5 stream from which fermentable C5 sugars can be recovered) and the solids component (C6 stream from which fermentable C6 sugars can be accessed).

The liquid component (C5 stream) comprises water, dissolved sugars (such as xylose, arabinose and glucose) to be made available for fermentation into ethanol, acids and other soluble components recovered from the hemicellulose. The solids component (C6 stream) comprises water, acids and solids such as cellulose from which sugar, such as glucose, can be made available for fermentation into ethanol, and lignin. According to an embodiment, the biomass material may comprise about 15 to 50 percent (dry weight) cobs, 35 to 65 percent (dry weight) leaves and husks, 10 to 30 percent (dry weight) stalk, and, in accordance with some embodiments, less than 5 percent (dry weight) foreign material. For alternative biomass sources, such as wood chips, the composition of the biomass may vary greatly. The moisture content of biomass varies, for example, based on harvest conditions, harvest timing, and storage conditions. The moisture content of example corn bales may vary from less than 20 percent to more than 40 percent. It would be beneficial to be able to control the moisture content of the biomass brought to the facility and the amount of water introduced into the ethanol production process, in these embodiments. It would also be beneficial to know the moisture content of the biomass, when biomass is purchased, because the price of the biomass is usually set on a dry matter basis. It would also be beneficial for farmers to be able monitor the moisture content of their biomass in storage. Note that biomass may often be collected into bales for transportation or storage purposes. It is intended that some embodiments of the moisture measurement apparatus are equally usable with biomass in baled form as well as loose biomass material.

Many assays exist for determining moisture content of plant materials, often comprising measuring weight loss during drying in an oven, for example. Measuring moisture content using an oven usually consumes considerable time and is not a portable method. Other methods include, for example, Near Infrared Spectroscopy (NIR), which requires expensive and sensitive equipment and is also not very suitable for field use. It would therefore be advantageous to provide for an apparatus, system, and method that can measure moisture content quickly and that can be made portable.

Figure 4:
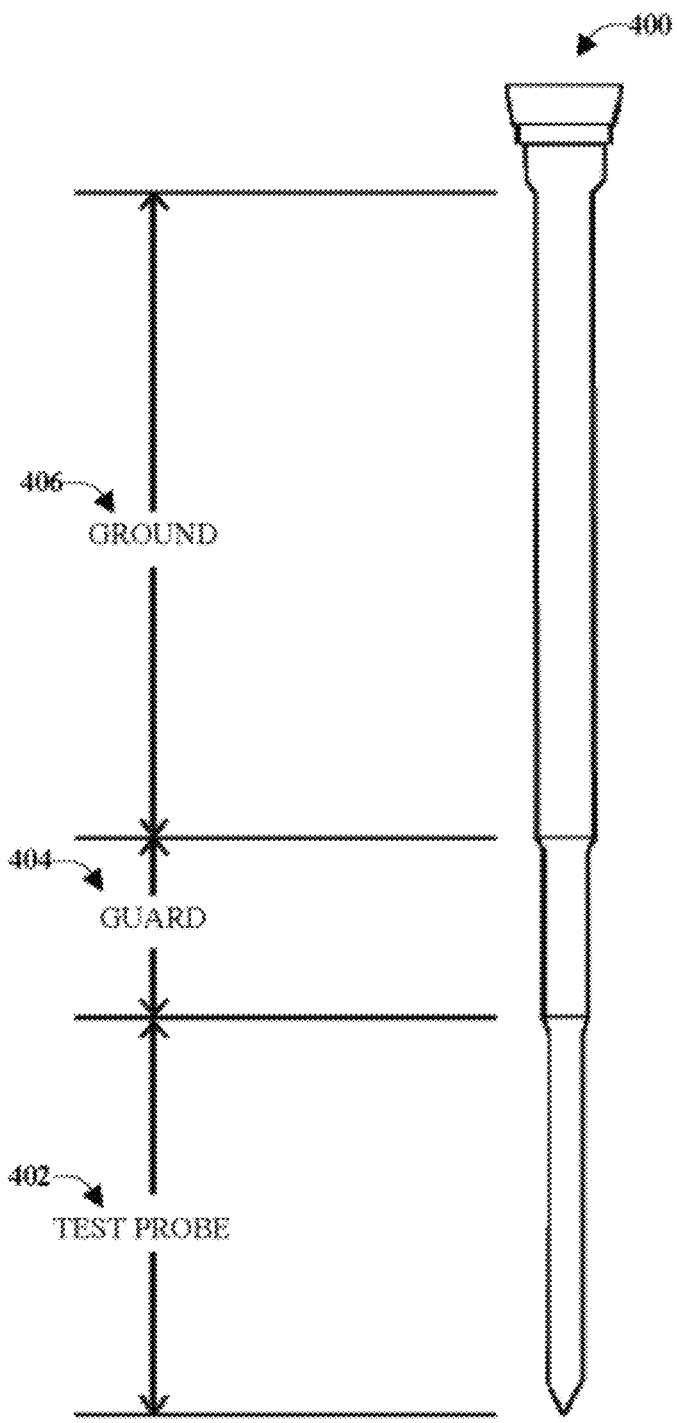
FIG. 4 is an example of a single probe apparatus for measuring moisture content, according to an embodiment.

In order to meet these long felt, and yet unmet, needs for a rapid, cost effective, and portable moisture measurement apparatus, FIG. 4 illustrates a single probe apparatus 400 for measuring moisture content, according to an embodiment. The single probe apparatus 400 can be inserted into biomass and can be used to measure the moisture content of the material. Biomass may include baled material, as well as loose biomass materials. In some embodiments, moisture content may be measured via a capacitance probe. The capacitance output (e.g. in mA units) can be converted to a moisture reading using various techniques (e.g., a calibration). According to an embodiment, as shown in FIG. 4, the single probe apparatus 400 may comprise a test probe section 402, a guard section 404, and a ground section 406. The length of the single probe apparatus 400 may be varied according to need and size of bales, and may be up to around 0.9 meters (around 3 feet) long, according to an embodiment. The test probe section 402 can be about 2.5 cm (about 1 inch) or longer, the guard section 404 may be about 2.5 to 7.5 cm (about 1 to 3 inches), and the ground section 406 can be at least around 2.5 cm (around 1 inch) or longer, but, in accordance with some embodiments, is at least about 30 cm (about 1 foot). According to alternative embodiments, the single probe apparatus 400 may comprise two or more guard sections.

Figure 5:
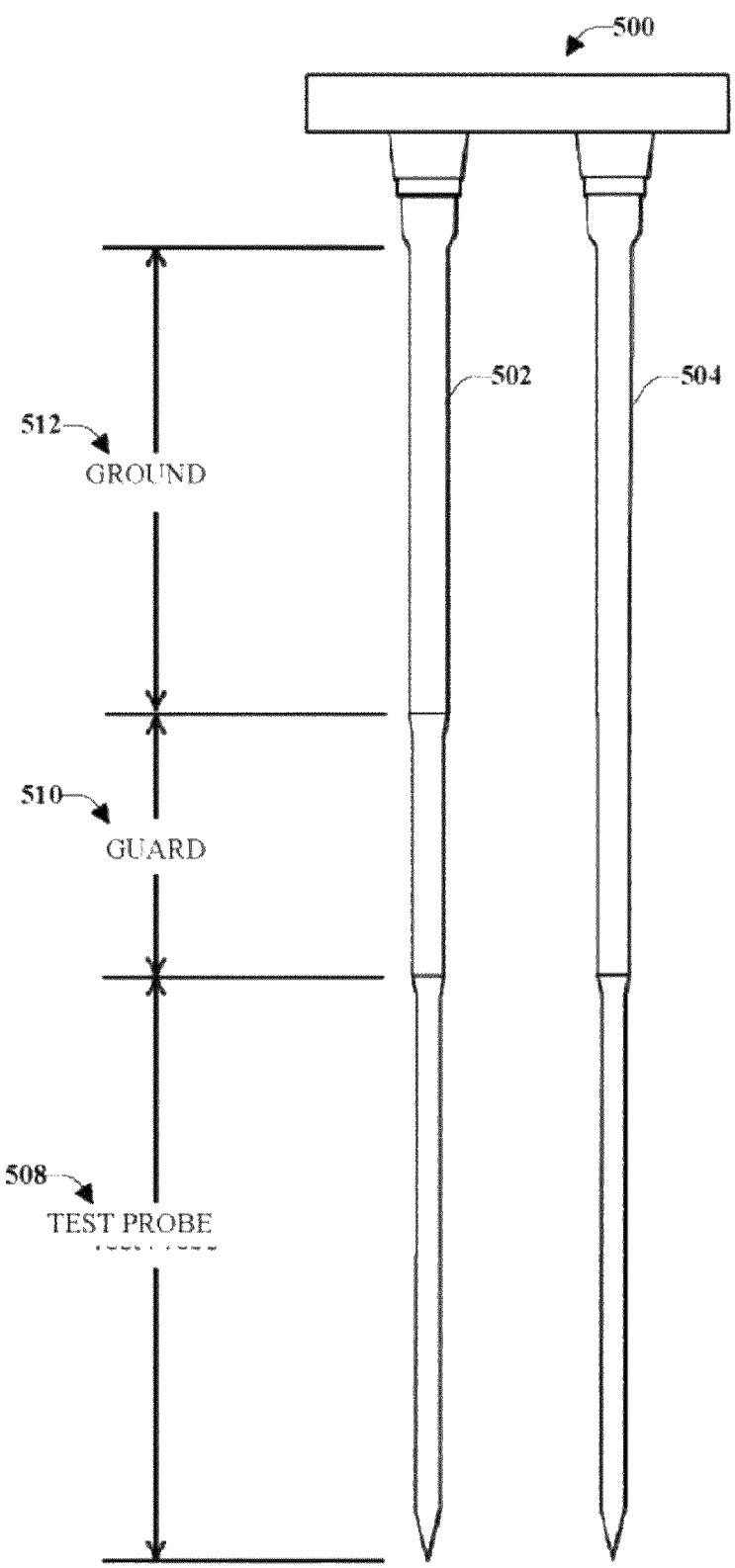
FIG. 5 is an example of a multi-probe apparatus for measuring moisture content, according to an embodiment.

According to another embodiment, as shown in FIG. 5, a multi-probe apparatus 500 for measuring moisture content can be utilized, according to an embodiment. The multi-probe apparatus 500 comprises two or more probes, according to an embodiment. In accordance with some aspects, a first probe 502 can be used as a test probe and a second probe 504 can be used as a ground or an inverted signal. Each probe 502, 504 can comprise a test probe section 508, a guard section 510, and a ground section 512. In accordance with some embodiments, two or more guard sections are utilized.

The general shape, materials, and construction of the probe (single probe or multi-probes) may vary, but should facilitate pushing the probe into a biomass bale and/or loose biomass materials. If two (or more) probes are used, the probes might be too flexible and a distance between the probes cannot remain constant, according to an embodiment. Note that while some embodiments discussed include capacitance measurement devices to determine moisture content, additional probes types are likewise considered as within the scope of some embodiments. For example, the probe may alternatively utilize microwave absorption, electrical resistance, and other known, or future known moisture measurement systems, in some embodiments.

The probe (or probes) can be mounted to (or operatively connected to) a device that facilitates positioning and/or inserting the probe(s) into biomass. For example, the probe(s) can be operatively connected to an arm (e.g., a hydraulic arm, a pneumatic arm, a truck probe arm, and so on). It should be noted that insertion of the test probe into biomass, particularly when in bale form, may require a substantial amount of force. As such, the selection of the mechanism for positioning the probe should take into consideration the forces required to properly insert the probe into the biomass, whether in bale form or otherwise. Hydraulic arms, such as those seen in FIG. 6 for example, may be particularly well suited for mounting the probe in some embodiments.

In according with an embodiment, the probe(s) take a reading that is indicative of a moisture content of the biomass (e.g., measurement by conductance, capacitance, and so forth). The reading can be taken automatically, semi-automatically, or based on other criteria, such as by request and/or manually.

According to an embodiment, the probe (or probes) is coupled to a reader that may render (in any perceivable format (e.g., visually, such as on a display, audibly, and so forth) the capacitance reading measured by the probe. In accordance with some aspects, the reader converts the capacitance reading to a moisture reading using a calibration that may be programmed into the reader and outputs the moisture reading in a perceivable format. According to some embodiments, the reader is located remote from the probe wherein signals from the probe are wirelessly transferred to the reader.

Figure 6:
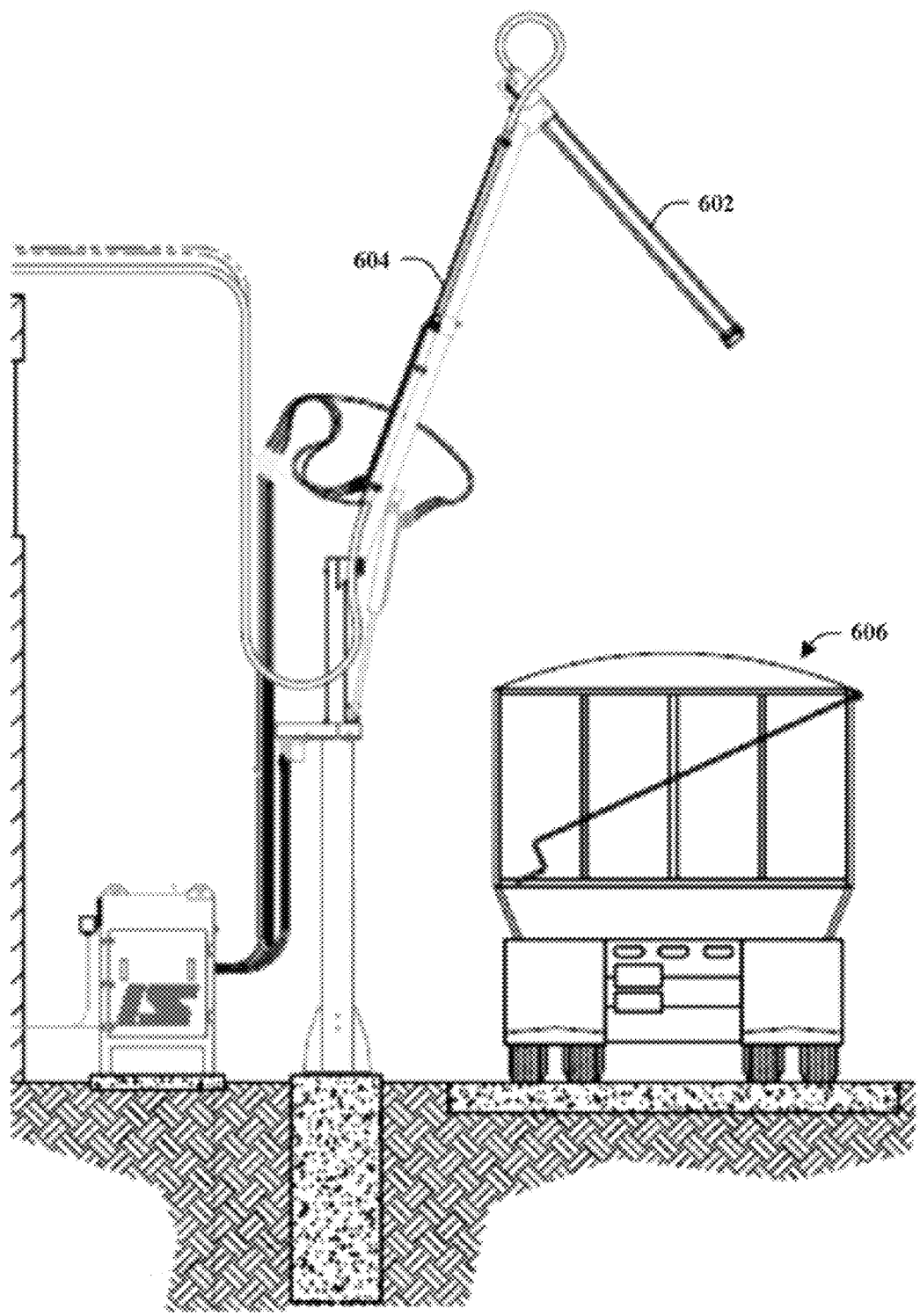
FIG. 6 is an example apparatus that can be utilized for measuring moisture content, in accordance with an embodiment.

According to an embodiment, as shown in FIG. 6, the probe 602 (or probes) may be mounted onto a hydraulic arm 604, for example, to test the moisture content of biomass bales as they are transported to a facility on a truck or a trailer 606. The trailer 606 can be positioned next to the hydraulic arm 604. The hydraulic arm 604 can be used to position the probe 602 over a biomass bale and to push the probe into the bale to measure the capacitance. The hydraulic arm 604 is illustrated as including two joints, and the central length may be extended or shortened by an operator. This can enable the arm to reach most locations of the exposed biomass in a truck or trailer. Note that other hydraulic, pneumatic, or actuator driven mounting devices are considered to be within the scope of some embodiments. Further, arms with more or fewer joints and/or the ability to rotate are all considered within the scope of some embodiments. The signal can be transmitted to a reader that converts the signal into a moisture reading using a calibration. The moisture reading can be output on a display or other device that is configured to output the moisture reading in a perceivable format.

A limited example was conducted according to an exemplary embodiment of the system in an effort to determine suitable apparatus and operating conditions for an apparatus for measuring moisture content.

EXAMPLE 1

Figure 7:
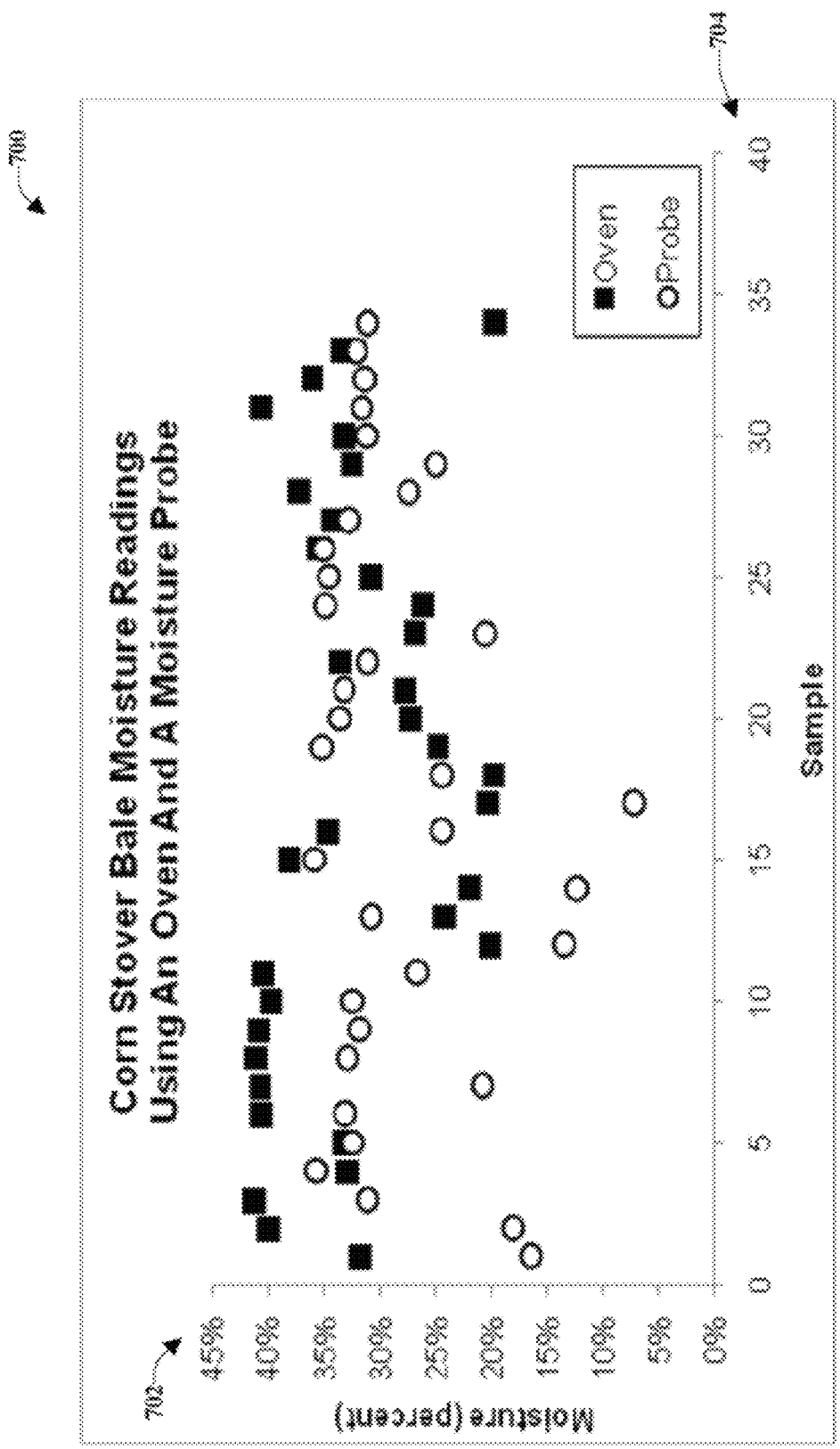
FIG. 7 is a graph illustrating the results of corn stover bale moisture readings using an oven and a moisture probe, according to a limited example.

The apparatus as shown in FIG. 6 was used in an experiment to test the functionality of the moisture measurement. The moisture of loose biomass (comprising approximately 72 to 92 percent corn cobs) was measured using a probe that had been calibrated with a three point calibration. Samples of the loose biomass were also tested for moisture using a microwave oven moisture method. The corn cob content of the samples was also determined. The results are shown in FIG. 7, which illustrates a graph 700, wherein a percentage of moisture 702 is shown along the vertical axis and the sample number 704 is shown along the horizontal axis. The measurements taken from the oven are shown by the filled squares and the measurements taken from the probe are shown by the circles.

It was observed that generally the moisture readings from the probe trended with the microwave oven moisture readings. It was also observed that the readings from the probe were generally lower than the readings from the microwave method. The error in the measurements was attributed mainly to the calibration, and could be significantly reduced by using a calibration with more data points, for example 20-50 data points. It was further observed that the composition of the loose biomass (the relative amount of cobs as compared to husks, leaves, and stalks) did not have an impact on the accuracy of the moisture readings from the probe.

The embodiments as disclosed and described in the application (including the FIGURES and Examples) are intended to be illustrative and explanatory of the various aspects. Modifications and variations of the disclosed embodiments, for example, of the apparatus and processes employed (or to be employed) as well as of the compositions and treatments used (or to be used), are possible; all such modifications and variations are intended to be within the scope of the disclosed aspects.

The word "exemplary" is used to mean serving as an example, instance, or illustration. Any embodiment or design described as "exemplary" is not necessarily to be construed as preferred or advantageous over other embodiments or designs, nor is it meant to preclude equivalent exemplary structures and techniques known to those of ordinary skill in the art. Rather, use of the word exemplary is intended to present concepts in a concrete fashion, and the disclosed subject matter is not limited by such examples.

The term "or" is intended to mean an inclusive "or" rather than an exclusive "or." To the extent that the terms "comprises," "has," "contains," and other similar words are used in either the detailed description or the claims, for the avoidance of doubt, such terms are intended to be inclusive in a manner similar to the term "comprising" as an open transition word without precluding any additional or other elements.

What is claimed is:

1. An apparatus for measuring moisture content of biomass, comprising:
   a probe apparatus having a first length comprising a probe structure consisting of a ground section coupled to a guard section, and a test probe section coupled to the guard section; wherein the first length, from 7.5 cm to 90 cm is the sum of lengths of the ground section, the guard section and the probe section and
   a mechanical arm that positions the probe apparatus over the biomass and inserts the probe apparatus into the biomass, wherein the probe apparatus measures moisture of the biomass, the mechanical arm having a plurality of joints so as to enable the mechanical arm to reach at least a majority of locations of the biomass;
   wherein the probe apparatus is mounted on the mechanical arm, and
   the mechanical arm is at least one of a hydraulically driven arm and a pneumatically driven arm.

2. The apparatus of claim 1, wherein the probe apparatus is configured to measure a capacitance of the biomass in order to measure the moisture content of the biomass.

3. The apparatus of claim 2, further comprising a reader that renders the capacitance measured by the probe apparatus.

4. The apparatus of claim 3, wherein the reader is located remote from the probe apparatus.

5. The apparatus of claim 2, further comprising a reader that converts the capacitance measured by the probe apparatus into a reading of the moisture, wherein the moisture reading is output by the reader.

6. The apparatus of claim 5, wherein the reader is located remote from the probe apparatus.

7. The apparatus of claim 1, wherein the probe apparatus is a multi-probe apparatus comprising at least two probe structures.

8. The apparatus of claim 7, wherein a distance between adjacent probe structures of the multi-probe apparatus remains constant.

9. The apparatus of claim 7, wherein a first probe structure of the multi-probe apparatus is a test probe and a second probe of the multi-probe apparatus is an inverted signal.

10. The apparatus of claim 1, wherein the mechanical arm inserts the probe apparatus into the biomass as the biomass is being transported in a trailer, wherein the mechanical arm is mounted to a platform separate from the trailer.

11. The apparatus of claim 1, wherein the biomass comprises biomass bales.

12. The apparatus of claim 11, wherein the mechanical arm pushes the probe apparatus into the biomass bales.

13. The apparatus of claim 1, wherein the mechanical arm is mounted on a vehicle.

14. A system for measuring moisture content, comprising:
   means for reading a moisture content of biomass, wherein the means for reading comprises a probe structure having a ground section coupled to at least one-guard section, and a test probe section coupled to the at least one guard section wherein lengths of the ground section, the at least one guard section and the test section comprise a first length of the probe structure, wherein the first length is from 7.5 cm to 90 cm;
   means for positioning over and inserting the means for reading into the biomass such that the means for reading can read the moisture content at most locations of the biomass, wherein the means for positioning and inserting comprises at least one of a hydraulically driven arm and a pneumatically driven arm.

15. The system of claim 14, further comprising:
   means for obtaining the moisture content reading after the means for reading is inserted into the biomass wherein the means for obtaining the moisture content comprises a display or other device configured to output the moisture reading in a perceivable format.

16. The system of claim 14, wherein the means for reading comprises a single probe structure.

17. The system of claim 14, wherein the means for reading comprises at least two probe structures.

18. A method for measuring moisture content of biomass, comprising:
   providing a device that can take a reading that is indicative of a moisture content of the biomass, the device comprising a probe structure having a ground section coupled to at least one guard section, and a test probe section coupled to a guard section wherein lengths of the ground section, the at least one guard section and the test section comprise a first length of the probe structure wherein the first length is from 7.5 cm to 90 cm;

positioning the device over the biomass by a mechanical arm such that the device can reach most locations of the biomass, wherein the mechanical arm is at least one of a hydraulically driven arm and a pneumatically driven arm;

inserting the device into the biomass by the mechanical arm; and obtaining the reading that is indicative of the moisture content.

19. The method of claim 18, wherein the providing comprises providing the device that includes at least one probe structure.

20. The method of claim 18, further comprises outputting the reading in a perceivable format.

* * * * *